United States Patent [19]

Corrigan et al.

[11] Patent Number: 4,803,956
[45] Date of Patent: Feb. 14, 1989

[54] CO-EXTRUSTION OF MULTI-COMPONENT INSECTICIDAL PET COLLARS

[75] Inventors: Eugene J. Corrigan, Chesterfield; Earl R. Atkinson, Jr., Mechanicsville, both of Va.

[73] Assignee: A. H. Robins Company, Incorporated, Richmond, Va.

[21] Appl. No.: 661,101

[22] Filed: Oct. 15, 1984

[51] Int. Cl.$^4$ ............................................. A01K 27/00
[52] U.S. Cl. ..................................... 119/106; 119/156
[58] Field of Search ................... 119/106, 156; 424/14, 424/16, 28

[56] References Cited

U.S. PATENT DOCUMENTS

| | | | |
|---|---|---|---|
| 3,904,746 | 9/1975 | Aries | 119/106 X |
| 3,978,820 | 9/1976 | Drehman | 119/106 |
| 4,031,859 | 6/1977 | Stewart | 119/106 |
| 4,150,109 | 4/1979 | Dick et al. | 119/106 X |
| 4,158,051 | 6/1979 | Greenberg et al. | 119/156 X |
| 4,218,991 | 8/1980 | Cole | 119/156 X |
| 4,224,901 | 9/1980 | Carey, Jr. | 119/106 |

FOREIGN PATENT DOCUMENTS 2050834 1/1981 United Kingdom ................ 119/156

Primary Examiner—Robert P. Swiatek

[57] ABSTRACT

Co-extruded insecticidal pet collars contain one or more active insecticidal components in a desired relationship to the skin of the animal. The outside layer (away from the skin) contains carbamate, organo-phosphate chlorinated hydrocarbon or other insecticide that is irritating to the skin, or a cholinesterase inhibitor. The inside layer acts as a barrier to the insecticide. The layers of a multi-layered collar which is prepared by extrusion may also contain different insecticidal systems. A co-extruded collar is prepared by preparing two blends which have varying concentrations of active and/or inert ingredients, depending on the end product which is desired. Each of the blends is fed into an extruder wherein the polyvinyl chloride is fused. The melt blend from extruder B is then transferred to the die of extruder A where it becomes an integral part of the extruded strip from extruder A.

9 Claims, 1 Drawing Sheet

CO-EXTRUSTION OF MULTI-COMPONENT INSECTICIDAL PET COLLARS

This invention relates to devices for protecting domestic animals against Ectoparasites, e.g., ticks and fleas, and more particularly relates to a flea and tick collar for providing protection to an animal.

Previously commercially marketed flea and tick collars have been manufactured from a monolithic matrix containing either one or two insecticides, these insecticides being dispersed uniformly throughout the polymeric matrix. In many such devices, the insecticide containing the polymer matrix is in direct contact with the skin of the cat or dog, and if two insecticides are utilized, both insecticides are dispersed together within the matrix. This construction can result in several problems: (1) because of the high degree of contact by an organophosphate or carbamate insecticide, abnormally high depression of cholinesterase or irritation of the skin in the animal occurs; (2) if the insecticides are mixed within the matrix, changes in the morphology of the plastic are caused so that the plastic becomes tacky with a distasteful odor. Such mixing also results in release rates which are not optimum for the insecticides, resulting in a less efficacious collar; (3) because a monolithic matrix requires a high concentration of insecticides to produce an effective collar, it is not economical to use a non-cholinesterase inhibiting, safer insecticide, such as the synthetic pyrethroids.

U.S. Pat. No. 4,224,901 discloses a combination in a flea-tick collar and an outer protective collar for animals and points out that the reason for this combination is to avoid direct contact of the skin of the animal with the chemicals in the flea and tick collars.

U.S. Pat. No. 3,978,820 is also directed toward solving the problem of direct contact of an animal's skin with the insecticide by providing a collar which holds an insecticide-impregnated strip while providing a physical barrier between the strip and the hair of the animal and the hair and skin of the animal.

U.S. Pat. No. 4,150,109 and U.S. Pat. No. 4,189,467 disclose an animal collar containing a polyurethane plus an insecticidal active compound and point out that it is possible to prepare animal collars based purely on polyurethane and then further states that in some cases it is desirable to impregnate and/or coat a suitable carrier (for example, a fabric made of natural material, such as cotton, and/or synthetic fibers, leather, imitation leather, or a porous or homogenous plastic sheet) with the polyurethane. It is also stated that carriers are worn on the outside of the collar, and the coating containing the polyurethane and the Ectoparasiticide is on the inside of the collar.

U.S. Pat. No. 3,904,746 is directed to a flea collar and teaches that a hollow band can be produced by extrusion or by joining two flat bands of low thickness by welding or by sewing. In the latter instance, one of the two bands, for example, that are intended to face the neck of the animal can be of an inert nature such as, for example, gauze, leather, or a polymer-like material.

U.S. Pat. No. 4,141,322 teaches a collar which has a strip of resin containing a solid pesticidal composition, this strip being laced through loops on the exposed surface of the collar which can be plastic.

The object of this invention is to prepare collars by co-extrusion, thereby eliminating many difficulties. The preferred co-extrusion methods are as follows: (1) co-extrusion of a collar in which an outside layer (away from the skin) contains carbamate, organophosphate chlorinated hydrocarbon or other insecticide that is irritating, or a cholinesterase inhibitor and in which an inside layer acts as a barrier to the insecticide; (2) co-extrusion of a multi-layered collar in which the different layers contain different insecticidal systems; and (3) co-extrusion of a multi-layered collar in which one layer contains a large concentration of an insecticide while the second layer contains no active ingredient.

The object of this invention is to prepare collars by co-extrusion, thereby eliminating many such difficulties.

It is another object to co-extrude a collar in which the outside layer (away from the skin) contains carbamate, organophosphate chlorinated hydrocarbon or other insecticide that is irritating, or a cholinesterase inhibitor and in which the inside layer acts as a barrier to the insecticide.

It is a further object to provide a multi-layered collar by co-extrusion in which the different layers contain different insecticidal systems.

It is an additional object to provide a multi-layered collar by co-extrusion in which one layer contains a large concentration of insecticide while the second layer contains no active ingredient.

The general procedure for preparing a monolithic polyvinyl chloride insecticide collar is to prepare a dry blend of materials containing all of the inert and active ingredients and then to extrude the blend through a die into a cooling bath. The resulting plastic strip is cut, buckled, and packaged.

The general procedure for preparing a co-extruded collar is to prepare two blends which have varying concentrations of active and inert ingredients, depending on the end product which is desired. Each of the blends is fed into an extruder wherein the polyvinyl chloride is fused. The melt blend from extruder B is then transferred to the die of extruder A where it becomes an integral part of the extruded strip from extruder A.

Figure 1:
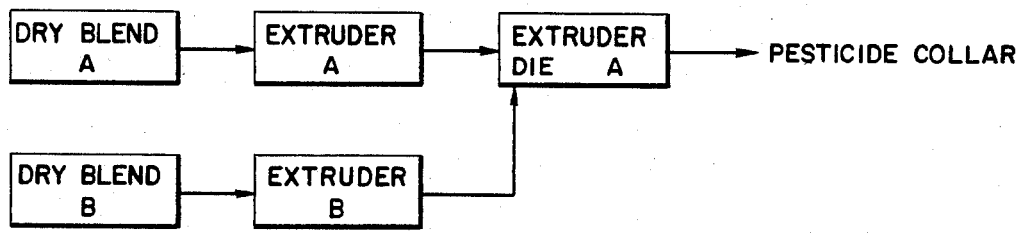
FIG. 1 is a schematic flow sheet for making a co-extruded collar wherein the plastic matrix and the barrier layer are essentially side by side.
Figure 2:
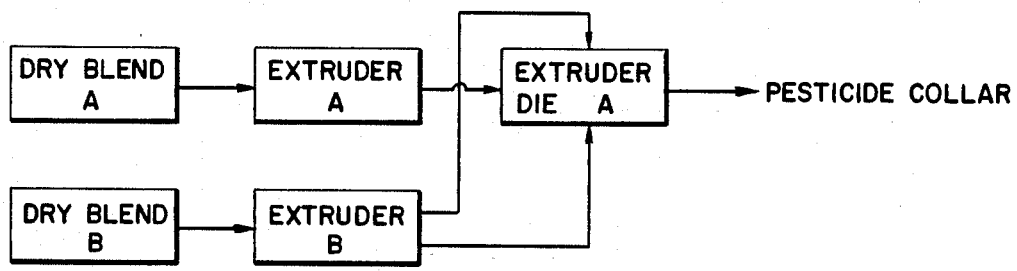
FIG. 2 is a schematic flow sheet for making a co-extruded collar wherein the plastic matrix is surrounded by a barrier layer.
Figure 3A:
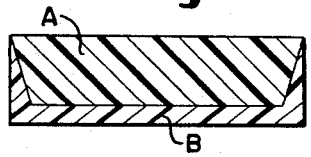
Figure 3D:
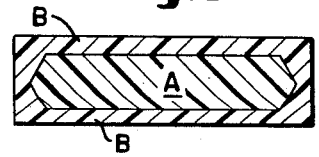
Figure 3B:
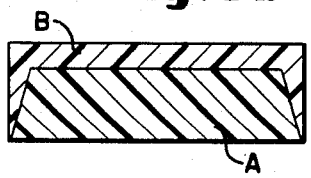
Figure 3E:
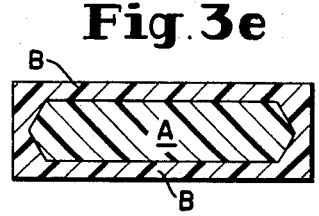

Six configurations of co-extruded collars which can be achieved by the process of this invention and in which the matrices and barrier layers are specifically identified are as follows:

FIG. 3a: (A) Plastic matrix with one or more insecticides, and (B) Plastic barrier layer, FIG. 3b: (A) Plastic matrix, and (B) Plastic matrix with high concentration of insecticide, FIG. 3c: (A) Plastic matrix with insecticide system, and (B) Plastic matrix with second insecticide system, FIG. 3d: (A) Plastic matrix with or without insecticide system, and (B) Plastic matrix with second insecticide system, FIG. 3e: (A) Plastic matrix, and (B) Plastic matrix with insecticide system, and FIG. 3f: (A) Plastic matrix with insecticide system, and (B) Plastic matrix.

Insecticidal agents which may be used are carbamates, organo-phosphorous compounds, organo-chlorine compounds, pyrethroids and mixtures thereof.

Carbamates useful in the compositions of the present invention are represented by the formula:

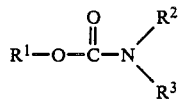

wherein $R^2$ is hydrogen or lower alkyl, $R^3$ is lower alkyl and $R^1$ is aryl, substituted aryl, heterocyclic or substituted heterocyclic groups.

The term "lower alkyl" as used herein refers to an alkyl group, branched or straight chain, having a chain length of one to six carbon atoms.

The term "aryl" as used herein refers to an aryl group such as phenyl or naphthyl.

The term "substituted aryl" as used herein refers to a phenyl or naphthyl group substituted with one or more groups such as lower alkyl, halogen, lower alkoxy, lower alkylamino, lower dialkylamino or lower alkylthio.

The term "heterocyclic" as used herein refers to an organic cyclic group having an oxygen atom, sulfur atom or nitrogen atom in the nucleus thereof and containing up to 12 carbon atoms.

The term "substituted heterocyclic" as used herein refers to a heterocyclic group substituted with one or more groups such as lower alkyl, lower alkoxy, lower alkylthio, lower alkylamino, lower dialkylamino or halogen.

Typical of the carbamates which can be used in the present invention are:
2,2-dimethyl-1,3-benzodioxal-4-OL methyl carbamate,
2-isopropylphenyl N-methyl carbamate,
2-isopropoxyphenyl N-methyl carbamate,
3-(1-methylbutyl)phenyl N-methyl carbamate,
3-(1-ethylpropyl)phenyl N-methyl carbamate,
6-chloro-, 3,4-xylenyl N-methyl carbamate,
4-methylthio-3,5-xylenyl N-methyl carbamate,
1-naphthyl N-methyl carbamate,
1-naphthyl N-ethyl carbamate,
1-naphthyl N-isopropyl carbamate,
1-naphthyl N-butyl carbamate,
1-naphthyl N-hexyl carbamate,
1-(4-chloronaphthyl) N-methyl carbamate,
1-(5,6-dihydronaphthyl) N-methyl carbamate,
1-(5,8-dihydronaphthyl) N-methyl carbamate,
4-benzothienyl N-methyl carbamate,
1-phenyl-3-methylpyrazol-5-yl N,N-dimethyl carbamate,
dimethyl carbamate,
2-(N,N-dimethyl carbamyl)-3-methylpyrazol-5-yl N,N-dimethyl carbamate, and
mixtures thereof. The preparation of carbamates of the above formula has been previously described. See, for example, U.S. Pat. Nos. 2,903,478 and 3,203,853.

Some useful alkyl-, alkaryl-, aralkyl- and heterocyclic carbamates are m-(1-ethylpropyl)phenyl methylcarbamate, m-(1-methylbutyl)phenyl methyl carbamate, 2-dimethylamino-5,6-dimethylpyrimidin-4-yl dimethylcarbamate, 4-methylthio-3,5 xylyl-N-methyl carbamate, 2-(2,3-dixolan-2 yl)phenyl-N-methylcarbamate, 3-isopropyl-5-methylphenyl-N-methylcarbamate, 4-dimethylamino-3-tolyl-N-methylcarbamate.

Useful organo-phosphorous compounds are phosphoric acid esters of the formula:

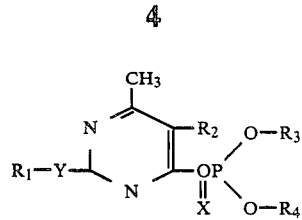

wherein $R_1$ represents a member selected from the group consisting of alkyl, alkenyl, alkoxylalkyl and alkyl-mercapto-alkyl radicals, $R_2$ represents a member selected from the group consisting of hydrogen, lower alkyl and low alkenyl radicals, $R_3$ and $R_4$ represent low alkyl radicals, X represents a member selected from the group consisting of oxygen and sulfur, and Y represents a member selected from the group consisting of the direct link and sulfur.

| Specific organo-phosphorous compounds are: | |
|---|---|
| Bromphos | Mevinphos |
| Phoxime | Crotoxyphos |
| "Phostex" | Phosphamidon |
| Temephos | Chlorfenvinphos |
| Iodofenphos | Fenitrothion |
| Pyrimiphos | Bromchlophos |
| Azidithion | Propetamphos |
| Ronnel | Tetrachlorvinphos |
| Malathion | Trichlorometaphos |
| Parathion | Fenthion |
| Azinphos | Fensulfothion |
| Butonate | Thionazin |
| Nichlorfos | Dithion |
| Crufomate | Endothion |
| Aspon | Mercaptophos |
| Chlorthion | Vamidothion |
| Fospirate | Dimethoate |
| Chlorpyrifos | Formothion |
| Trichlorphon | Ethion |
| Aldimithion | Phtalophos |
| Azothoate | Diazinon |
| Phosphinon | |
| II-Pyrethroids | |
| Barthrin | Fluvalinate |
| Bioresmethrin | Phenothrin |
| Tetrametrin | Alphamethrin |
| Resmethrin | Fenvalerate |
| Natural Pyrethrin | Cyfluthrin |
| Allethrin | Kadethrin |
| Cypermethrin | Flucythrinate |
| Permethrin | Cyprothrin |
| Decamethrin | Cyhalothrin |
| III-Organo-chlorine compounds | |
| Bromocyclene | TDE |
| Ethylane | Dienochlor |
| Methoxychlor | "Dilan" |
| Oxythioquinox | Chlorfenethol |

The composition according to the invention comprises 2–25% by weight of the insecticidal agent and more usually 2–15%.

Figure 3C:
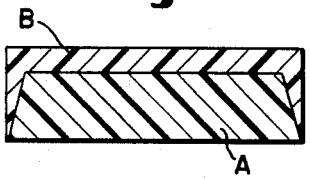
Figure 3F:
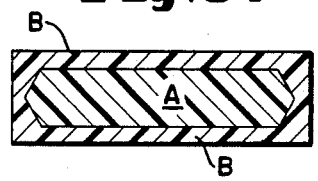

The following examples furnish comparative data for co-extruded collars having the configuration of FIG. 3c and containing insecticides, extruded monolayer collars containing comparable insecticides, and extruded monolayer collars without insecticides and tested as placebos. Ingredients in the blends of each formula are on weight basis.

EXAMPLE 1

Two sets of collars were prepared, using the formulas for preparing dry blends as shown in Table 1. Collar I was prepared by co-extrusion, utilizing the blends shown in Table 1 by co-extruding polybutylene terephthalate onto Blend A in the weight ratio of 1 to 20 and in the cross sectional configuration illustrated in FIG. 3C. Collar II was prepared by extruding Blend A, as shown in FIG. I, as a solid collar. A placebo collar was also prepared, having all of the ingredients of Blend A except for the insecticidal materials.

These three collars were tested by placing 6 of each type of insecticidal collar and 6 placebo collars on 18 dogs. The plasma cholinesterase of each dog was then determined periodically over a 28-day period, using standard techniques. The plasma cholinesterase activity is shown in Table 2. The percentage cholinesterase inhibition, calculated as in Table 3, indicates that the effect of pesticide on cholinesterase is inhibited by the use of the barrier.

TABLE 1

Formulas for Preparing Dry Blends

|  | Collar I | | | | |
|---|---|---|---|---|---|
|  | Blend A % | Blend B % | Average % | Collar II | Placebo |
| Polybutylene Terephthalate |  | 100 | 5.00 |  |  |
| Polyvinyl Chloride | 56.12 |  | 53.30 | 56.12 | 60.63 |
| Plasticizer | 24.61 |  | 23.37 | 24.27 | 35.11 |
| Epoxidized Soybean Oil | 3.01 |  | 2.86 | 3.01 | 3.01 |
| Stabilizer (Argus 565A) | 1.00 |  | 0.95 | 1.00 | 1.00 |
| Fragrance | 0.25 |  | 0.24 | 0.25 | 0.25 |
| Vapona | 10.50 |  | 9.98 | 10.82 | — |
| Chlorpyrifos | 4.51 |  | 4.28 | 4.51 | — |
| Actual Content |  |  |  |  |  |
| Vapona |  |  | 10.19 | 10.95 | 0.0 |
| Chlorpyrifos |  |  | 4.28 | 4.54 | 0.0 |

TABLE 2

Plasma Cholinesterase Activity (mcm/ml/min)

|  |  | Days | | | | |
|---|---|---|---|---|---|---|
|  | Pre-Test | 3 | 7 | 13 | 21 | 28 |
| Collar I | 3.32 | 2.12 | 1.78 | 1.43 | 1.45 | 1.60 |
| Collar II | 2.96 | 1.22 | 1.00 | 0.95 | 1.05 | 1.18 |
| Control | 3.25 | 3.20 | 3.27 | 2.80 | 2.82 | 3.02 |

TABLE 3

% Inhibition of Plasma Cholinesterase[1]

|  |  | Days | | | | |
|---|---|---|---|---|---|---|
|  | Pre-Test | 3 | 17 | 13 | 21 | 28 |
| Collar I | 0.0 | 35.7 | 45.5 | 56.0 | 55.5 | 50.5 |
| Collar II | 0.0 | 57.5 | 65.0 | 67.0 | 65.0 | 59.0 |
| Control | 0.0 | 1.5 | 0.0 | 11.2 | 10.5 | 4.5 |

[1] % Inhibition = $\frac{\text{Pre-test Cholinesterase} - \text{Cholinesterase at Day N}}{\text{Pre-Test Cholinesterase}} \times 100$

EXAMPLE 2

Two sets of insecticide-containing collars were prepared. Collar III was prepared by co-extrusion of Blend B onto one surface of Blend A, as shown in Table 4 and with the configuration of FIG. 3C, at a ratio of one part Blend B to 7.76 parts of Blend A. Collar IV was prepared by extruding Blend A, including the insecticides, and the placebo collar was prepared by extruding Blend A, without the insecticides.

Six of each type of insecticide-containing collar and six placebo collars were placed on 18 dogs. The plasma cholinesterase levels of these dogs were determined periodically over a 28-day period. The plasma cholinesterase activity is shown in Table 5, and the precent inhibition of cholinesterase is shown in Table 6, indicating that the barrier activity effectively reduced the effect of the insecticide.

EXAMPLE 3

Two sets of insecticide-containing collars were prepared by utilizing the formula shown in Table 7. Collar V was prepared by co-extruding Blends A and B in the ratio of one part of Blend B to 6.92 parts of Blend A. Collar VI was prepared by extruding Blend A, including the insecticides.

Six of each of these collars were placed on 12 dogs, and the dogs were infested with 100 fleas on eight different occasions. The dead fleas found in the pans under the animals were counted 24 hours after the infestations. The results are shown in Table 8. As can be seen from Table 8, co-extruded collar V had greater efficacy than the conventional matrix collar VI.

TABLE 4

Formula for Preparing Dry Blends

|  | Collar III | | | | |
|---|---|---|---|---|---|
|  | Blend A % | Blend B % | Average % | Collar IV | Placebo |
| Polyvinyl Chloride | 56.13 | 73.33 | 58.05 | 57.13 | 60.63 |
| Diisodecyl Phthalate | 24.62 | 22.11 | 24.34 | 26.30 | 35.11 |
| Epoxidized Soybean Oil | 3.00 | 3.01 | 3.00 | 3.00 | 3.01 |
| Stabilizer (Argus 565A) | 1.00 | 1.00 | 1.00 | 1.00 | 1.00 |
| Fragrance | 0.25 | 0.25 | 0.25 | 0.25 | 0.25 |
| Titanium dioxide | — | 0.40 | 0.05 |  | — |
| Vapona (Technical) | 10.00 | — | 8.87 | 7.81 | — |
| Chlorpyrifos (Technical) | 5.00 | — | 4.44 | 4.51 | — |
| Actual Assay |  |  |  |  |  |
| Vapona |  |  | 8.8 | 7.5 | 0.0 |
| Chlorpyrifos |  |  | 4.3 | 4.6 | 0.0 |

TABLE 5

Plasma Cholinesterase Activity (mcm/ml/min)

|  | Pre-Test | Days | | | |
|---|---|---|---|---|---|
|  | 0 | 7 | 14 | 21 | 28 |
| Collar III | 6.57 | 4.05 | 3.65 | 3.95 | 3.78 |
| Collar V | 6.47 | 2.78 | 2.53 | 2.78 | 2.49 |
| Placebo | 5.67 | 5.75 | 5.65 | 5.77 | 5.75 |

TABLE 6

% Inhibition of Plasma Cholinesterase

|  | Days | | | |
|---|---|---|---|---|
|  | 7 | 14 | 21 | 28 |
| Collar III | 38.5 | 44.4 | 39.9 | 42.4 |
| Collar IV | 57.0 | 60.9 | 57.0 | 61.5 |

TABLE 7

|  | Collar V | | Total | Collar VI |
|---|---|---|---|---|
|  | Blend A % | Blend B % | Collar % |  |
| Polyvinyl Chloride | 57.55 | 50.00 | 56.00 | 53.15 |
| Diisodecyl Phthalate | — | — | — | 17.50 |
| Dioctyl adipate | 13.00 | 30.25 | 15.18 | — |
| Epoxidized Soybean Oil | 3.00 | — | 2.62 | 3.06 |
| Stabilizer |  |  |  | 0.51 |
| Brown Pigment | 0.23 | — | 0.20 | 0.21 |
| Titanium dioxide | — | 0.75 | 0.09 | — |

TABLE 7-continued

|  | Collar V | | Total | |
|---|---|---|---|---|
|  | Blend A % | Blend B % | Collar % | Collar VI |
| Naled, Technical | 23.36 | — | 20.41 | 20.40 |
| Sendran, Technical | 2.86 | 19.00 | 4.90 | 4.91 |
| Actual Assay |  |  |  |  |
| Naled |  |  | 16.9 |  |
| Sendran |  |  | 4.5 |  |

TABLE 8

|  | Dead Fleas Found After 24 Hours | |
|---|---|---|
| Infestation No. | Collar V | Collar VI |
| 1 | 245 | 232 |
| 2 | 431 | 494 |
| 3 | 465 | 313 |
| 4 | 566 | 431 |
| 5 | 400 | 390 |
| 6 | 433 | 439 |
| 7 | 618 | 520 |
| 8 | 392 | 266 |
| Mean x̄ = | 444 | 386 |

EXAMPLE 4

Two sets of collars, collars VII and VIII, were prepared by utilizing the formula shown in Table 9. Collar VII was prepared by co-extruding Blend A and Blend B in the ratio of 1 part of Blend B to 9 parts of Blend A by weight, again using the cross sectional configuration illustrated in FIG. 3C. The extruded collar VIII was prepared by using the blend similar to Blend A, shown in Table 9 under its designation. The placebo collar was also extruded with the blend shown beneath this designation at the right hand side of collar IX, without any insecticide.

Six of the collars which had been prepared by using the formula for collar VII were applied to cats, with the insecticide layer next to the animals' skins (High Contact), and six were applied to the cats with the insecticide layer away from the animals' skins (Low Contact). Six of the matrix collars (collar VIII), with insecticide dispersed throughout the plastic matrix, were also applied to cats. Finally 6 placebo collars containing no insecticide were applied to cats as controls. One hundred fleas were placed on each animal once a week for three weeks, without removal of existing fleas, so that the number of applied fleas was cumulative. The number of dead fleas in pans under the animals were counted at six hours post infestation, as shown in Table 10, and the number of live fleas on the animals' bodies was counted four days following infestation, as shown in Table 11. The results shown in Tables 10 and 11 are the average for cats. As indicated, co-extruded collar VII was more effective than matrix collar VIII.

TABLE 9

|  | Collar VII | | | | |
|---|---|---|---|---|---|
|  | Blend A % | Blend B % | Average % | Collar VIII | Placebo |
| Polyvinyl Chloride | 55.63 | 50.25 | 55.12 | 58.86 | 60.63 |
| Diisodecyl Phthalate | 40.11 | 10.30 | 37.12 | 34.09 | 35.11 |
| Epoxidized Soybean Oil | 3.01 | 2.57 | 2.97 | 2.92 | 3.01 |
| Argus 565A Stabilizer | 1.00 | 1.71 | 1.07 | 0.97 | 1.00 |
| Fragrance | 0.25 | — | 0.22 | 0.25 | 0.25 |
| Titanium |  | 0.34 | 0.03 |  |  |

TABLE 9-continued

|  | Collar VII | | | | |
|---|---|---|---|---|---|
|  | Blend A % | Blend B % | Average % | Collar VIII | Placebo |
| dioxide |  |  |  |  |  |
| Hi Sil 233 | — | 9.10 | .91 |  | — |
| Sumithrin | 25.73 | 2.57 | 2.91 |  | — |
| Assay |  |  |  |  |  |
| Sumithrin |  | 2.58 | 2.4 |  |  |

TABLE 10

|  | Dead Fleas After 6 Hours | | | |
|---|---|---|---|---|
|  | Collar VII | | Collar VIII | |
| Infestation | Low Contact | High Contact | Matrix | Control |
| 1 | 15 | 8 | 10 | 0 |
| 2 | 29 | 59 | 28 | 3 |
| 3 | 64 | 195 | 116 | 9 |
| x̄ | 36 | 87 | 51 | 6 |

TABLE 11

| Efficacy 5 Days Post-Infestation Live Fleas On Cats | | | | |
|---|---|---|---|---|
| 1 | 33 | 52 | 111 | 252 |
| 2 | 53 | 74 | 67 | 286 |
| x̄ | 43(84) | 63(77) | 89(67) | 269 |

( ) % Efficacy

EXAMPLE 5

Collar IX was prepared by co-extruding Blend A and Blend B in the weight ratio of 9.5 to 1.0, using the blend shown in Table 12.

Six collars of collar IX type were placed on six cats, and six placebo collars prepared according to Table I were placed on six additional cats. One hundred fleas were placed on each cat once a week for four weeks. The number of dead fleas in the pans under the cats were determined six hours after infestation, and the number of live fleas on the cats were determined on the fifth day following infestation. The results shown in Tables 13 and 14 indicate that collar IX was effective in controlling fleas.

In the process of co-extruding the polymers used as matrices and barrier layers, it is only necessary that the temperatures used be above the melting points of both polymers and that the polymers be compatible with each other. The preferred temperature range is 150°-180° C.

Table 15 shows the extruder conditions used for extruding collars I–IX that are described in Examples 1–5.

Although polyvinyl chloride was used in the examples for the insecticidal blends, other polymers known in the art, such as polymers and copolymers of vinyl chloride, vinyl acetate, vinyl acetals, vinyl alcohol, vinylbenzene and divinylbenzene and vinylidene chloride are satisfactory. The copolymers may contain additional components such as ethylenic, propylenic, butadienic, isopronic, acrylic and methacrylic components.

Preferably, the polymer or copolymer of a vinyl compound is a polyvinyl halide and contains one or more plasticizers.

The plasticizers are liquid esters with a vapor pressure of less than 0.001 mm/Hg at 25° C. Some nonrestrictive examples of plasticizers are: diethyl, dimethyl, dipropyl, dibutyl, dihexyl, dioctyl, and didecyl phthalate, dibutyl, diamyl, dinonyl, dioctyl, and didecyl adipate, dipropyl, dibutyl, dibenzyl and dioctyl sebacate, diethyl, dipropyl and dibutyl citrate, triphenyl and tricresyl phosphate and the triglycerides.

The preferred plasticizers are dioctyl phthalate, diisodecyl phthalate and dioctyl adipate. Suitable stabilizers are all those known from diazinone, of which the following can be mentioned: epoxides such as epichlorohydrin, calcium, magnesium, zinc, tin, barium, cadmium or potassium stearate, the laurates and palmitates of these same metals, chlorinated terphenyls and butoxy-propylene-glycol. The preferred stabilizers are calcium or zinc stearate and epoxidized soya bean oil.

TABLE 12

| | Collar IX | | |
|---|---|---|---|
| | Blend A % | Blend B % | Average % |
| Polyvinyl Chloride | 60.32 | 59.13 | 56.24 |
| Diisodecyl Phthalate | — | 34.86 | 31.54 |
| Epoxidized Soybean Oil | — | 3.01 | 2.72 |
| Argus 565A Stabilizer | 2.89 | 1.00 | 1.18 |
| Hi Sil 233 | 5.43 | | 0.52 |
| Fragrance | — | 0.25 | 0.23 |
| Sumithrin, Technical | 31.36 | — | 2.99 |
| Vapona, Technical | — | 1.75 | 1.58 |
| Actual Assay | | | |
| Sumithrin | | | 3.0 |
| Vapona | | | 1.0 |

TABLE 13

| | Dead Fleas After 6 Hours | |
|---|---|---|
| Infestation | Collar IX | Placebo |
| 1 | 109 | 3 |
| 2 | 60 | 3 |
| 3 | 56 | 6 |
| 4 | 229 | 29 |
| x̄ | 114 | 10 |

TABLE 14

| | Live Fleas on Cats on 5th Day Post Infestation | |
|---|---|---|
| Infestation | Collar IX | Placebo |
| 1 | 3 | 155 |
| 2 | 77 | 213 |
| 3 | 7 | 289 |
| 4 | 9 | 172 |
| x̄ | 24 (88.4) | 207 |

( ) % Efficacy

TABLE 15

Extruder Conditions Used to Produce Flea & Tick Collars*

| | Placebo Extruder A | I Extruder A | I Extruder B | II Extruder A | III Extruder A | III Extruder B | IV Extruder A | V Extruder A | V Extruder B | VI Extruder C** | VII Extruder A | VII Extruder B | VIII Extruder A | IX Extruder A | IX Extruder B |
|---|---|---|---|---|---|---|---|---|---|---|---|---|---|---|---|
| Temperature, °F. | | | | | | | | | | | | | | | |
| Zone 1 | 300 | 300 | 460 | 300 | 300 | 350 | 300 | 300 | 300 | 255 | 300 | 300 | 300 | 300 | 350 |
| Zone 2 | 300 | 300 | 500 | 300 | 300 | 350 | 300 | 300 | 300 | 260 | 300 | 300 | 300 | 300 | 350 |
| Zone 3 | 300 | 300 | 495 | 300 | 300 | 350 | 300 | 300 | 350 | 265 | 300 | 300 | 300 | 300 | 350 |
| Zone 4 | | | | | | | | | | 270 | | | | | |
| Zone 5 | | | | | | | | | | 275 | | | | | |
| Die | 350 | 385 | 500 | 385 | 350 | 375 | 340 | 350 | 335 | 275 | 310 | 350 | 340 | 350 | 370 |
| Total Throughout lbs/hr | 53 | 54 | | 50 | 53 | | 48 | 56 | | 110 | 48 | | 42 | 50 | |
| Extruder AMPs | 28 | 29 | 3.8 | 29 | 29 | 5.2 | 28 | 34 | 2.8 | 25 | 24 | 3.8 | 26 | 31 | 4 |
| Extruder RPM | 62.5 | 62.5 | 13.5 | 62.5 | 62.5 | 40.5 | 62.5 | 62.5 | 47.3 | 50 | 62.5 | 47.3 | 62.5 | 62.5 | 46 |
| Collar 10 | 198-222 | 529-143(20) | | 529-143(1) | 773-78 | | 529-120 | 773-91 | | Lot No. A1084034B | 773-26 | | 773-29 | 773-39 | |

Co-extruded collars I, III, V, VII, and IV were produced by feeding extruder A with blend A and extruder B with blend B.
Typical production conditions.
A - Polymer Lab 2 in. Welex extruder
B - Polymer Lab 1¼ in. Wayne extruder
C - Production 2½ in. Davis standard extruder

What is claimed is:

1. An animal collar for controlling fleas and ticks on an animal, comprising a plastic matrix containing at least one insecticide and a plastic barrier layer, said matrix and said layer being co-extruded.

2. The collar of claim 1, wherein said barrier layer surrounds said matrix on three sides.

3. The collar of claim 2, wherein said matrix is on the inside of said collar, next to the skin of an animal wearing said collar.

4. The collar of claim 2, wherein said barrier layer is next to said animal's skin.

5. An animal collar for controlling fleas and ticks on an animal which comprises a first plastic matrix containing a first insecticide and a second plastic matrix containing a second insecticide, said matrices being co-extruded.

6. The collar of claim 5, wherein said first plastic matrix containing said first insecticide surrounds said second plastic matrix containing said second insecticide on three sides.

7. The collar of claim 6, wherein said second plastic matrix containing said second insecticide surrounds said first plastic matrix containing said first insecticide on three sides.

8. The plastic collar of claim 6, wherein said second plastic matrix containing said second insecticide surrounds said first plastic matrix containing said first insecticide on four sides.

9. A collar for controlling fleas and ticks on an animal which comprises a plastic barrier layer surrounding a plastic matrix containing an insecticide system on all sides thereof, said layer and said matrix being co-extruded.

* * * * *